(12) United States Patent
Salvermoser et al.

(10) Patent No.: US 9,173,695 B2
(45) Date of Patent: Nov. 3, 2015

(54) BONE FASTENER ASSEMBLY INSTRUMENT

(71) Applicant: PARADIGM SPINE, LLC, New York, NY (US)

(72) Inventors: Markus Salvermoser, Tuttlingen-Mohringen (DE); Stephan Eckhof, Rietheim-Weilheim (DE); Sven Oliver Muckenfuss, Spaichingen (DE); Jason E. Garber, Las Vegas, NV (US)

(73) Assignee: PARADIGM SPINE, LLC, New York, NY (US)

( * ) Notice: Subject to any disclaimer, the term of this patent is extended or adjusted under 35 U.S.C. 154(b) by 210 days.

(21) Appl. No.: 13/949,574

(22) Filed: Jul. 24, 2013

(65) Prior Publication Data

US 2014/0031830 A1   Jan. 30, 2014

Related U.S. Application Data

(60) Provisional application No. 61/675,222, filed on Jul. 24, 2012, provisional application No. 61/784,254, filed on Mar. 14, 2013.

(51) Int. Cl.
| | |
|---|---|
| *A61B 17/88* | (2006.01) |
| *A61B 17/70* | (2006.01) |
| *A61B 17/68* | (2006.01) |
| *A61B 17/86* | (2006.01) |

(52) U.S. Cl.
CPC ......... *A61B 17/8875* (2013.01); *A61B 17/7068* (2013.01); *A61B 17/683* (2013.01); *A61B 2017/867* (2013.01)

(58) Field of Classification Search
CPC ............... A61B 17/8875; A61B 17/88; A61B 17/8891; A61B 17/8894
See application file for complete search history.

(56) References Cited

U.S. PATENT DOCUMENTS

| | | | | |
|---|---|---|---|---|
| 3,604,487 | A * | 9/1971 | Gilbert | 81/443 |
| 4,033,043 | A * | 7/1977 | Cunningham | 33/806 |
| 5,133,715 | A * | 7/1992 | Lenzo | 606/60 |
| 5,226,906 | A * | 7/1993 | Crombie et al. | 606/916 |
| 5,236,053 | A * | 8/1993 | Butsch | 173/176 |
| 5,445,641 | A * | 8/1995 | Frigg et al. | 606/86 R |
| 5,458,603 | A * | 10/1995 | Futch, Sr. | 606/104 |
| 5,626,474 | A * | 5/1997 | Kukla et al. | 433/141 |
| 5,997,545 | A * | 12/1999 | Doherty et al. | 606/102 |
| 6,330,845 | B1 * | 12/2001 | Meulink | 81/462 |
| 6,436,123 | B1 * | 8/2002 | Magovern | 606/216 |
| 6,511,484 | B2 * | 1/2003 | Torode et al. | 606/104 |
| 6,669,698 | B1 * | 12/2003 | Tromanhauser et al. | 606/86 A |
| 6,752,832 | B2 * | 6/2004 | Neumann | 623/17.15 |
| 7,207,995 | B1 * | 4/2007 | Vandewalle | 606/104 |
| 7,563,275 | B2 * | 7/2009 | Falahee et al. | 606/328 |
| 7,608,094 | B2 * | 10/2009 | Falahee | 606/247 |
| 7,922,750 | B2 * | 4/2011 | Trautwein et al. | 606/279 |

(Continued)

FOREIGN PATENT DOCUMENTS

| | | |
|---|---|---|
| DE | 19828137 | 1/2000 |
| WO | 2007021850 | 2/2007 |

*Primary Examiner* — Christian Sevilla
(74) *Attorney, Agent, or Firm* — MH2 Technology Law Group, LLP

(57) ABSTRACT

A bone fastener assembly instrument that can assemble a two-component bone fastener during surgery is provided. The bone fastener may be of a type that comprises a threaded bolt and nut for securing an implantable device to bone, such as a spinous process. A method for using the bone fastener assembly instrument is also provided.

15 Claims, 12 Drawing Sheets

(56) References Cited

U.S. PATENT DOCUMENTS

| | | | |
|---|---|---|---|
| 8,002,812 B2* | 8/2011 | Falahee et al. | 606/328 |
| 8,105,329 B2* | 1/2012 | Brumfield et al. | 606/86 A |
| 8,167,885 B2* | 5/2012 | Barrett | 606/86 A |
| 8,216,241 B2* | 7/2012 | Runco et al. | 606/86 A |
| 8,323,292 B2* | 12/2012 | Dudasik et al. | 606/96 |
| 8,685,065 B1* | 4/2014 | Taber et al. | 606/279 |
| 2003/0040746 A1* | 2/2003 | Mitchell et al. | 606/61 |
| 2003/0236529 A1* | 12/2003 | Shluzas et al. | 606/105 |
| 2004/0106927 A1* | 6/2004 | Ruffner et al. | 606/90 |
| 2005/0137608 A1* | 6/2005 | Hearn et al. | 606/103 |
| 2008/0140125 A1* | 6/2008 | Mitchell et al. | 606/279 |
| 2009/0259262 A1* | 10/2009 | Nayet | 606/86 A |
| 2010/0076490 A1* | 3/2010 | Greenwald et al. | 606/279 |
| 2010/0262198 A1* | 10/2010 | Braunschweiler et al. | 606/86 A |
| 2011/0034961 A1* | 2/2011 | Runco et al. | 606/86 A |
| 2011/0040341 A1* | 2/2011 | Stad et al. | 606/86 A |
| 2011/0106091 A1* | 5/2011 | Fisher et al. | 606/88 |
| 2011/0172722 A1* | 7/2011 | Verhulst et al. | 606/86 A |
| 2011/0190819 A1* | 8/2011 | Trautwein et al. | 606/249 |
| 2011/0224740 A1* | 9/2011 | Smisson et al. | 606/86 A |
| 2011/0313323 A1* | 12/2011 | Henderson et al. | 600/594 |
| 2011/0319936 A1* | 12/2011 | Gordon et al. | 606/248 |
| 2012/0253413 A1 | 10/2012 | Runco et al. | |
| 2012/0277810 A1* | 11/2012 | Siccardi et al. | 606/86 A |
| 2012/0310292 A1 | 12/2012 | Smisson, III et al. | |
| 2013/0066385 A1* | 3/2013 | Benoist | 606/86 A |
| 2013/0096625 A1* | 4/2013 | McClintock et al. | 606/279 |
| 2014/0031830 A1* | 1/2014 | Salvermoser et al. | 606/104 |
| 2014/0249591 A1* | 9/2014 | Peultier et al. | 606/86 A |

* cited by examiner

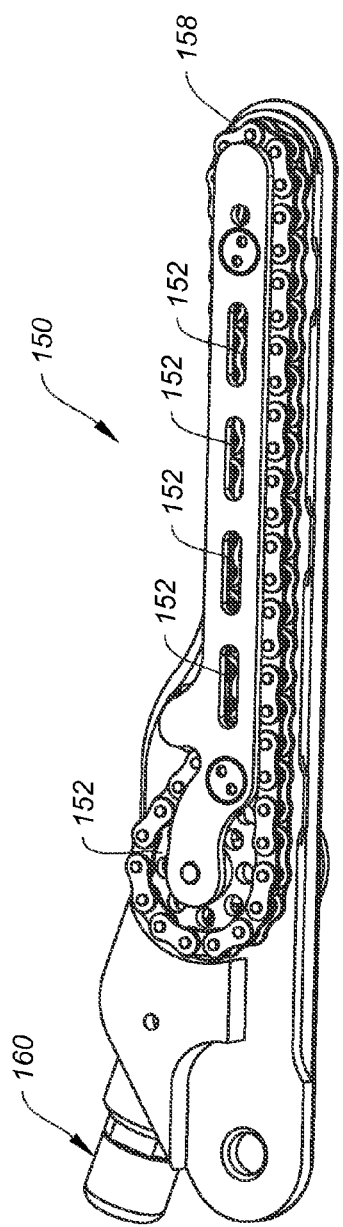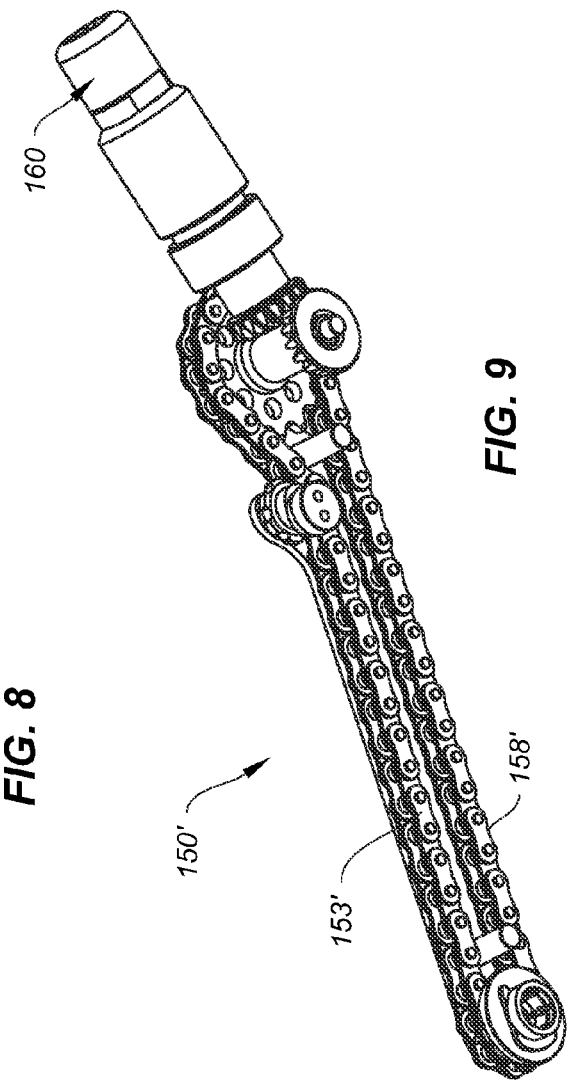
FIG. 8
FIG. 9

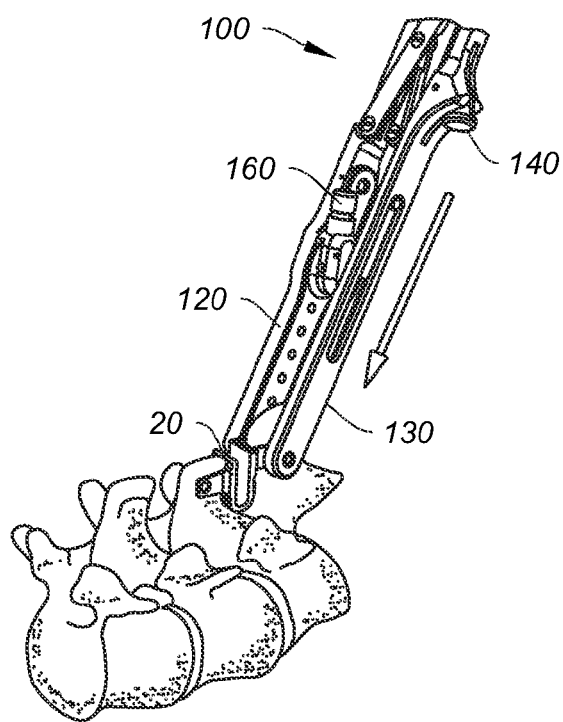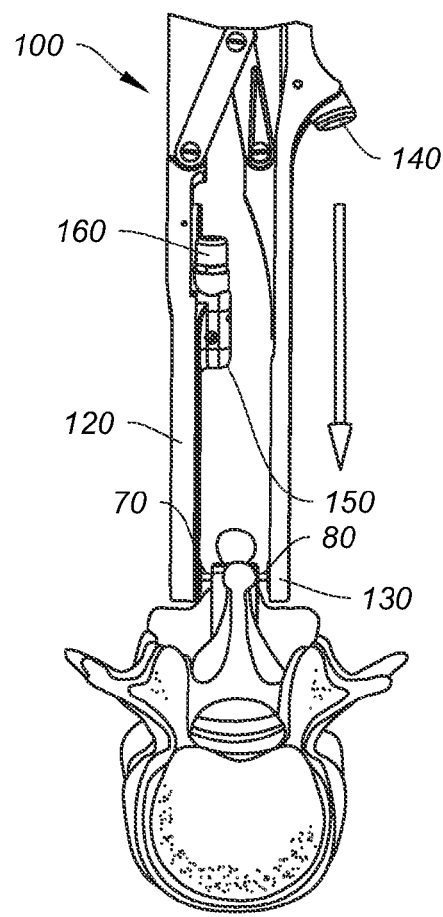
FIG. 10F
FIG. 10G

BONE FASTENER ASSEMBLY INSTRUMENT

CROSS-REFERENCE TO RELATED APPLICATIONS

This application claims priority to U.S. Provisional Application No. 61/675,222 filed Jul. 24, 2012, and U.S. Provisional Application No. 61/784,254 filed Mar. 14, 2013, both entitled "BONE FASTENER ASSEMBLY INSTRUMENT", the contents of which are incorporated herein by reference in their entirety.

FIELD

The present invention relates to medical instruments for use during surgery, and more particularly to an instrument for assembling a fastener between an implantable device and bone.

BACKGROUND

Diseases of the spine cause significant morbidity. These diseases include abnormalities of the vertebrae, the intervertebral discs, the facet joints, and connective tissue around the spine. These abnormalities can be due to a number of causes, including mechanical injury or degenerative disc disease. Such abnormalities can cause instability to the spine, allowing the vertebral column to become misaligned and producing micromotion between adjacent vertebrae. Vertebral misalignment and micromotion may result in wear to the vertebral bony surfaces and ultimately cause severe pain. Further, these conditions are often chronic and progressive problems.

The treatments for spinal disorders can include long-term medical management or surgery. Medical management is generally directed at controlling the symptoms, such as pain, rather than correcting the underlying problem. For some patients, this may require chronic use of pain medications, which may alter patient mental state or cause other negative side effects.

Recently, a variety of interspinous stabilization devices have become available. These devices may be implanted between the spinous processes of two or more adjacent vertebrae. By stabilizing the spinous processes in this way, significant stress may be taken off the intervertebral discs to prevent disease progression or to improve conditions such as spinal stenosis. In addition, vertebral motion may be controlled without severely altering spinal anatomy.

Currently available interspinous stabilization systems can be secured between adjacent spinous processes using a number of different mechanisms. For example, such devices can include sharp barbs or other surface projections that engage the bony surface of a spinous process. In addition, flexible ligaments or sutures can be placed around the implants and adjacent bone. However, it may be desirable to provide a more rigid and secure attachment to the spinous processes. For example, a rigid attachment may be desirable to prevent the interspinous device from migrating or slipping out of position. In addition, a rigid attachment may be desirable to limit movement and promote fusion at a selected vertebral level. Even further, it may be desirable to provide a device that can also fit interlaminarly between adjacent vertebrae, thereby enhancing the stability of the region.

An interlaminar-interspinous vertebral stabilization system that can be easily implanted and can be securely attached to the spinous processes while being seated interlaminarly is disclosed in U.S. Pat. No. 7,922,750. The vertebral stabilization system utilizes a bone fastener to secure the system to bone. The bone fastener comprises two separate, engageable components that are assembled together during the implantation process. An insertion tool, along with a tightening instrument, is provided for the assembly of the bone fastener.

It would be desirable to provide an improved insertion tool that can be used to assemble the bone fastener of this system, as well as other systems, having a slim profile for ease of use. It would further be desirable to provide such an improved insertion tool enabling a shorter assembly time while also being compatible with the same components and tools available with this system.

SUMMARY

The present disclosure describes a bone fastener assembly instrument that can assemble a two-component bone fastener during surgery. The bone fastener may be of a type that comprises a threaded bolt and nut for securing an implantable device to bone, such as a spinous process. A method for using the bone fastener assembly instrument is also provided.

One aspect of the disclosure relates to an assembly instrument that properly aligns the threaded screw and nut during assembly of the bone fastener through an aperture of an implantable device, thus allowing the bone fastener to secure the implantable device to bone. In one exemplary embodiment, an instrument for assembling a two-component bone fastener is provided. The instrument may comprise a pair of handles, each handle extending into an arm terminating in a working end configured to hold a component of the bone fastener. The instrument may also include a spring bias mechanism between the handles.

In addition, a transmission mechanism may be provided for rotating one of the components of the bone fastener. This transmission mechanism may comprise a transmission mechanism in one embodiment, such as a series of gear wheels. In another embodiment, the transmission mechanism may comprise a chain, such as a rollerchain. These transmission mechanisms drive a drive train, such as a drive chain, that effects actuation of other parts such as screw holding components of the instrument.

The transmission mechanism may be configured to be releasably connected to the instrument. A catch and release mechanism for maintaining one of the arms in a retracted position during insertion and an expanded position during assembly may also be provided.

BRIEF DESCRIPTION OF THE DRAWINGS

The accompanying drawings, which are incorporated in and constitute a part of this specification, illustrate several embodiments of the disclosure and together with the description, serve to explain the principles of the disclosure.

FIG. 8 shows a perspective view of an exemplary embodiment of a transmission mechanism comprising gear wheels.

FIG. 9 shows a perspective view of an exemplary embodiment of a transmission mechanism comprising a rollerchain.

FIGS. 10A-10I illustrate an exemplary method of using the bone fastener assembly instrument of the present disclosure to assemble the bone fastener of FIG. 1B to the interlaminar-interspinous vertebral stabilization system of FIG. 1A.

It is to be understood that both the foregoing general description and the following detailed description are exemplary and explanatory only, and are not restrictive of the disclosure, as claimed. Additional features of the disclosure will be set forth in part in the description which follows or may be learned by practice of the disclosure. The features of the disclosure will be realized and attained by means of the elements and combinations particularly pointed out in the appended claims.

DESCRIPTION OF THE EMBODIMENTS

Figure 1A:
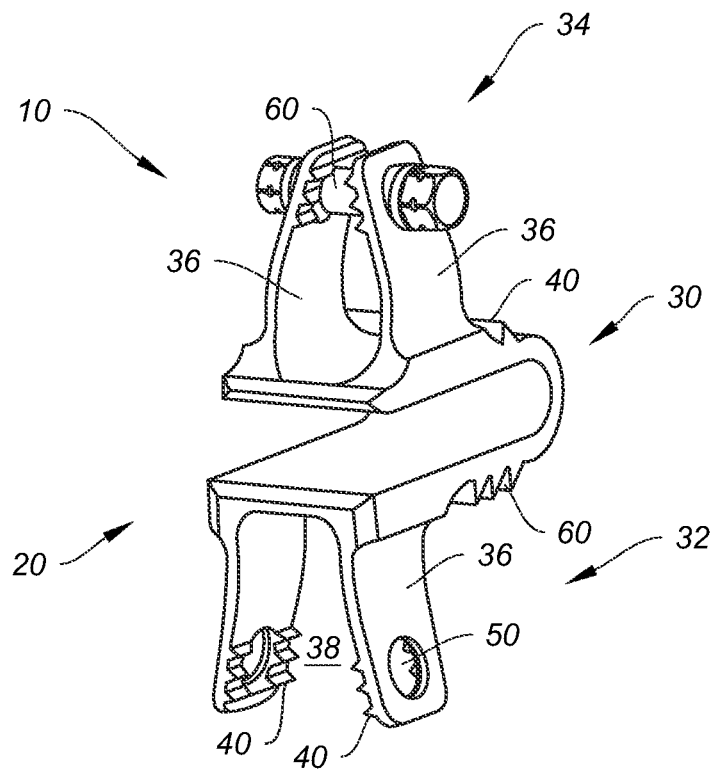
FIG. 1A is a perspective view of an exemplary embodiment of an interlaminar-interspinous vertebral stabilization system of the prior art.
Figure 1B:
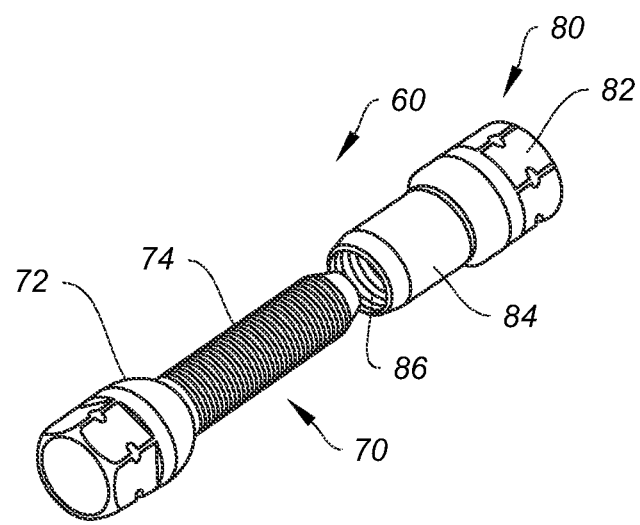
FIG. 1B is an enlarged exploded view of a bone fastener of the prior art usable with the interlaminar-interspinous vertebral stabilization system of FIG. 1A.

FIG. 1A shows an implantable interlaminar-interspinous vertebral stabilization system 10 for stabilizing adjacent vertebrae and FIG. 1B shows a bone fastener for use with the stabilization system 10, both of which are disclosed in U.S. Pat. No. 7,922,750. The prior art system 10 comprises an implantable device 20 configured for placement between the spinous processes of adjacent vertebrae. The system 10 can include one or more bone anchors 60 for securing the device 20 to spinous processes. Further, in one embodiment, the bone anchors 60 can rigidly fix the device 20 with respect to the spinous processes, thereby limiting movement at a selected vertebral level and promoting fusion at that level.

The device 20 may include a spacer body. The spacer body 20 may have various shapes and thicknesses, and can be produced from a variety of different materials. In one embodiment, the spacer body 20 may include a midsection 30 extending between an inferior section 32 and a superior section 34, as shown in FIG. 1A. When implanted in a patient, the superior section 34 is configured to contact a portion of a first spinous process, while the inferior section 32 is configured to contact a portion of a second, adjacent spinous process. In one embodiment, the midsection 30, inferior section 32, and superior section 34 may together form a substantially U-shaped spacer body 20, as shown. The spacer body 20 may be configured to be flexible and/or bendable, such as, for example, by providing an extendable and/or compressible midsection 30. The midsection 30 can act as a flexible hinge, allowing the superior section 34 and inferior section 32 to move away from or towards one another. Furthermore, the U-shaped spacer body enables the device 10 to be positioned, or fitted, interlaminarly after implantation, thereby enhancing the stabilization of the adjacent vertebrae.

To engage the spinous processes of adjacent vertebrae, the spacer body 20 may be provided with a pair of lateral walls or brackets 36 that extend from the inferior and superior sections 32, 34, as shown in FIG. 1A. Each of the pair of lateral walls 36 defines a stirrup 38 for receiving a spinous process. The spacer body 20 can be provided with lateral walls 36 of various sizes or heights to accommodate variations in patient anatomy. Likewise, the lateral walls 36 of different spacer bodies 20 may be provided at differing locations along the length of the inferior section 32 or superior section 34. The surgeon can thus select a suitably shaped and sized spacer body 20 depending on the particular vertebral level to be supported and the anatomy of the patient.

Further, the lateral walls 36 may also be adjustable with respect to the spacer body 20. For example, in one embodiment, the lateral walls 36 may be formed of a malleable material such that, after implantation, the surgeon may compress the lateral walls 36 together to reduce the gap between the lateral walls 36, thereby securely fixing the spacer body 20 to a spinous process located therein. In addition, the lateral walls 36 may be spread apart to facilitate insertion, as illustrated with the inferiorly located lateral wall 36 of FIG. 1A. The lateral walls 36 may be compressed or spread apart, for example, using surgical pliers or forceps.

The lateral walls or brackets 36 of the present invention can also include an aperture 50 for receiving a bone fastener to fix the brackets 36 to the spinous process. Such fastening members can ensure that the brackets 36 are pressed flat and/or securely against the spinous process in order to avoid any play of the brackets 36 with respect to the process. Further, the system 10 may act as a fusion-promoting device when the implantable device 20 is fastened to the spinous process in this manner.

As shown in FIG. 1B, the bone fastener 60 can be of a two-component type that includes a bolt 70 comprising a head 72 and a threaded, elongate body 74. To secure the bolt 70 within an aperture 50, a nut 80 is provided having a head 82, body portion 84, and threaded inner cavity 86 for receiving the threaded, elongate body 74 of the bolt 70. As the nut 80 is threaded onto the bolt 70, the lateral walls 36 may be drawn together. Thus, the bone fastener 60 and spacer body 20 may form a tight, secure connection with the spinous process. In some embodiments, the tight, secure connection between the body 20 and adjacent spinous processes will limit movement at the selected vertebral level, thereby promoting fusion at that level. In other embodiments, the nut 80 and bolt 70 may be tightened sufficiently to prevent the spacer body 20 from moving out of position between the spinous processes, but may be left sufficiently loose so as to allow a small amount of play between the spacer body 20 and spinous processes, so as not to promote fusion, or cause fusion to occur more slowly. Further, in some embodiments, the system 10 can include two bone fasteners 60, so that both the inferior and superior lateral walls 36 can be securely fastened to spinous processes. Thus, it is contemplated that the device 20, when positioned between the spinous processes of two adjacent vertebrae, may be secured to one spinous process and not the other spinous process, or to both adjacent spinous processes.

Figure 2:
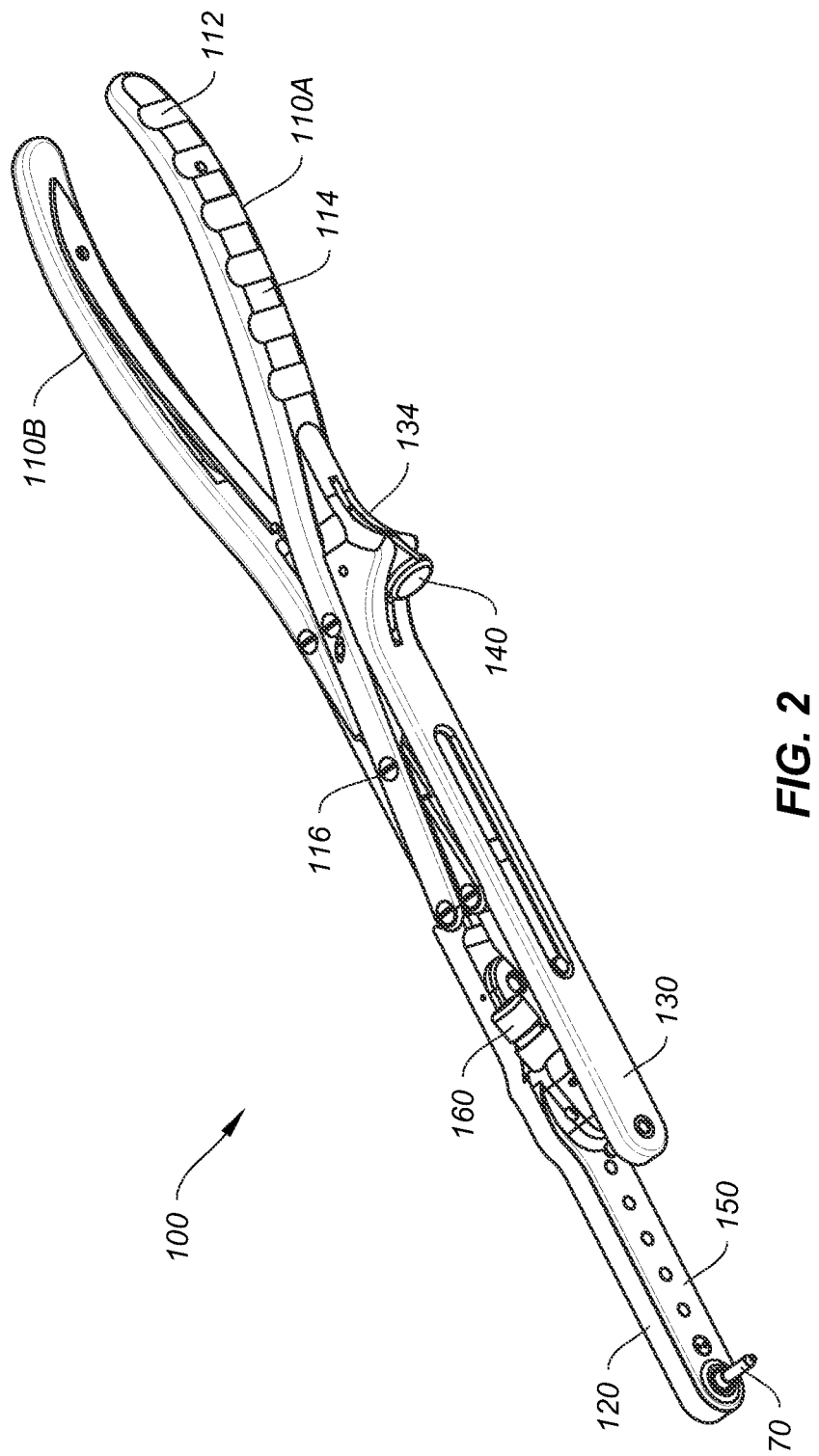
FIG. 2 is a perspective view of an exemplary embodiment of a bone fastener assembly instrument of the present disclosure in a collapsed configuration.
Figure 3:
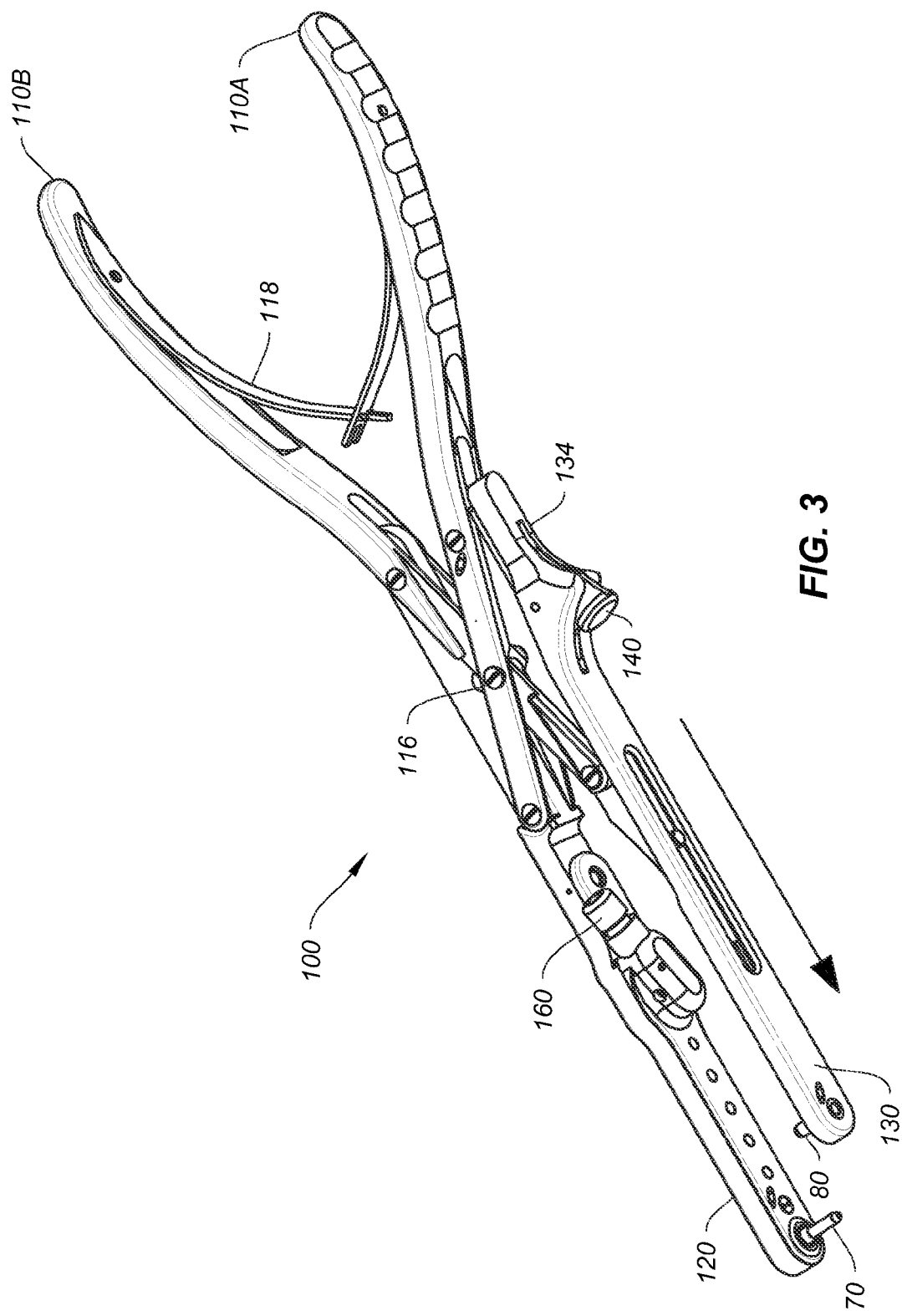
FIG. 3 is a perspective view of the bone fastener assembly instrument of FIG. 2 in a partially expanded configuration.
Figure 4:
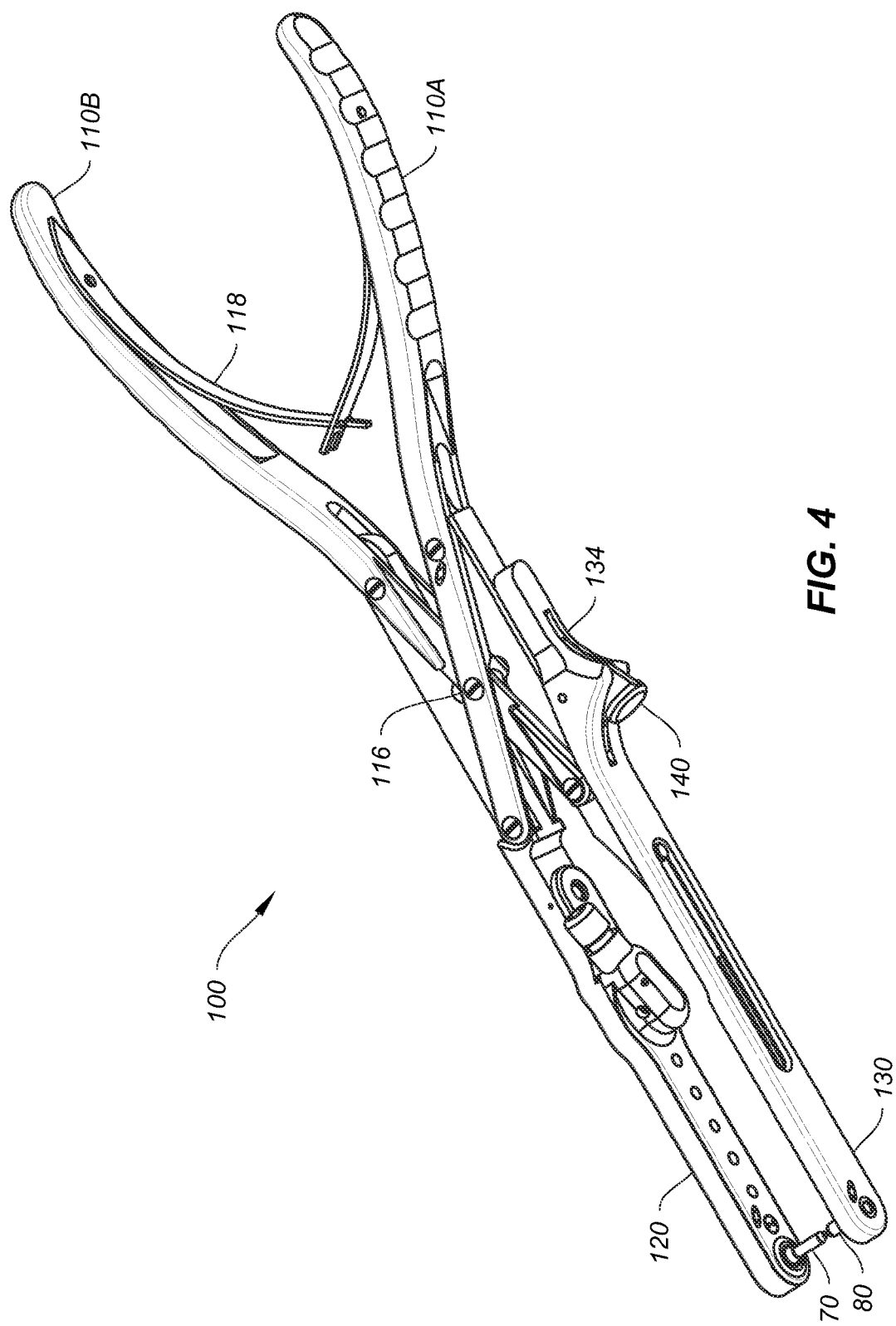
FIG. 4 is a perspective view of the bone fastener assembly instrument of FIG. 2 in a fully expanded configuration.

Turning now to FIGS. 2 to 4, a bone fastener assembly instrument 100 of the present disclosure is shown. The instrument may be useful for assembling the bone fastener 60 during implantation of the system 10. The insertion tool 100 may comprise a pair of handles 110A, 110B extending into gripping portions 112. The gripping portions 112 may include a surface modification such as for example bumps or raised portions 114 to provide a secure gripping surface for the user. The handles 110A, 110B are connected to one another with a pivotable hinge 116 in a manner similar to scissors or pliers, much like the hinge described with the insertion tool of U.S. Pat. No. 7,922,750. A leaf spring 118 may be positioned between the handles 110A, 110B, as further shown.

Extending distally from the handles 110A, 110B are arms that include a holding portion at their free ends for holding one component of the two-component bone fastener 60. Handle 110A extends into first arm 120. The first arm 120 includes an actuation or transmission mechanism 150, shown in greater detail in the exploded view of FIG. 7. The actuation or transmission mechanism 150 may be detachable. The first arm 120 may contain a depressed or cutaway portion 122 that allows the transmission mechanism 150 to fit inside the arm 120.

In one embodiment, the transmission mechanism 150 may include a series of gear wheels 152 that are actuated by means of port 160. As shown in greater detail in FIG. 8, the gear wheels are configured to move a drive train 158, which can be configured as a drive chain, for example.

FIG. 9 illustrates another exemplary embodiment of a transmission mechanism 150' that may be used interchangeably with transmission 150. As shown, the transmission mechanism 150' may comprise a rollerchain 153' that can be actuated by means of port 160, similar to gear wheels 152 of FIG. 8. Like the gear wheels 152, rollerchain 153' may be configured to move drive train 158'. The transmission mechanism 150' of the assembly instrument 100 may be configured to work without friction under load. The assembly instrument 100 with the transmission mechanism 150' would offer the user the ability to close the bone fastener 60 without crimping the wings 36 of the implantable device 10. Still in other examples, a drive belt or Cardan shaft may also be implemented as part of the transmission mechanism of the present disclosure.

Turning back to FIG. 7, the transmission mechanism 150 may include an aperture 154 that allows it to snap fit onto a depressible button 124 on the first arm 120. At the opposite end of the transmission mechanism 150 is a first component holding portion 156 for holding one of the components of the bone fastener 60. As shown in FIGS. 2 to 4, the first component holding portion 156 may be configured to hold onto the bolt 70.

Figure 6:
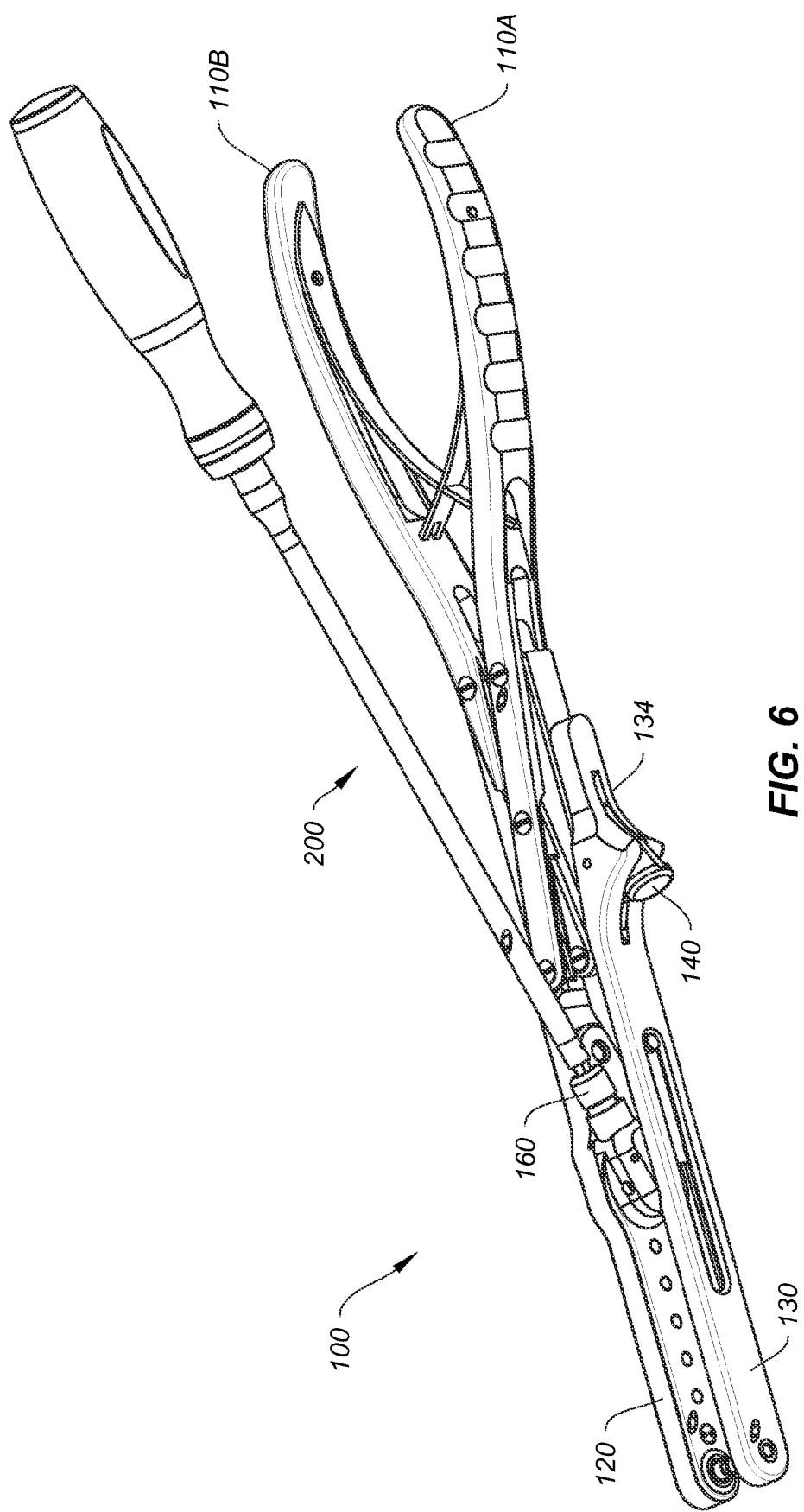
FIG. 6 is a perspective view of the bone fastener assembly instrument of FIG. 4 in cooperation with a tightening tool of the prior art.

The transmission mechanism 150 includes a port 160 configured to receive a tightening instrument 200, shown in FIG. 6. The tightening instrument 200 may be of the type provided in U.S. Pat. No. 7,922,750 and configured to fit complementarily within port 160, to actuate the transmission mechanism 150 and cause rotation of the bolt 70.

Handle 110B extends into a rail 170 onto which a second arm 130 may slidably connect. The second arm 130 may include a second component holding portion 136 for holding the nut 80 of the bone fastener 60. Additionally, second arm 130 may also include a projection 134 or finger rest that serves to move the second arm 130, which can include notches that ratchet along the outside of the handle 110A against the raised portions 114. The notches help to keep the instrument 100 in the locked or collapsed configuration. Like first arm 120, the second arm 130 may also be snap-fitted into place with the spring button 174 on the rail 170 and released by depressing a release button 140 on the instrument 100.

Figure 5A:
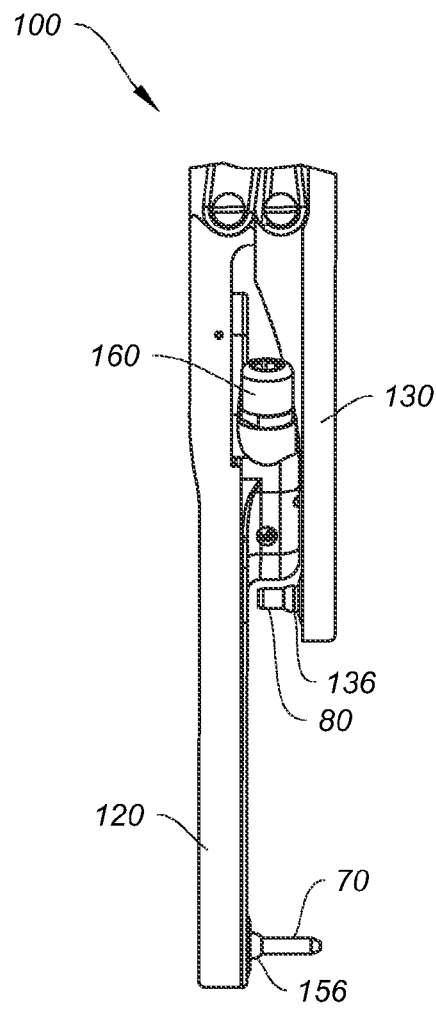
FIG. 5A is a partial top-down view of the bone fastener assembly instrument of FIG. 2.
Figure 5B:
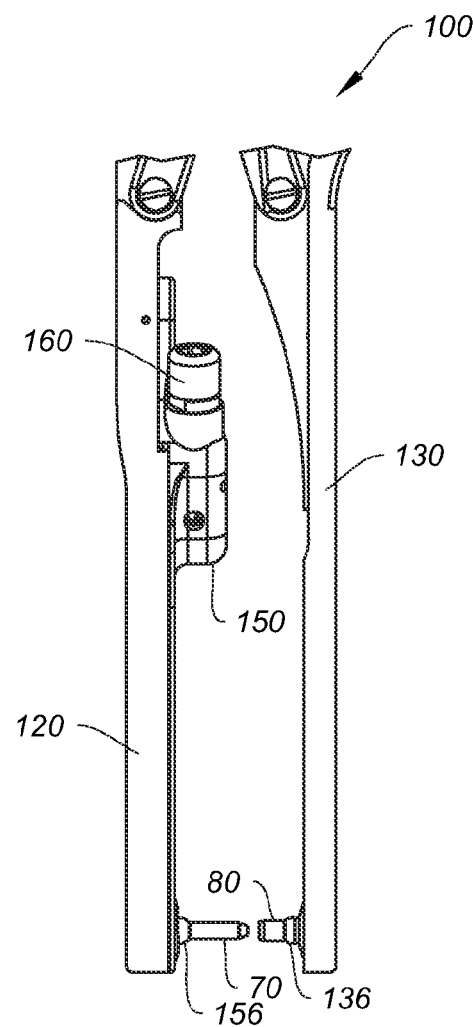
FIG. 5B is a partial top-down view of the bone fastener assembly instrument of FIG. 4.

The present bone fastener assembly instrument 100 is collapsible, able to be fully disassembled for sterilization, and allows for a quicker, more streamlined approach to assembling a bone fastener, such as the two-component rivet of the prior art described herein. More importantly, the instrument 100 provides a space-saving solution to assembly of the bone fastener. FIGS. 2 and 5A show the instrument 100 in a collapsed, or closed, position, wherein the width of the instrument 100 is in the range of about 15-25 mm, and preferably about 19 mm. FIG. 3 illustrates the manner in which the instrument 100 can be expanded, or opened. As shown by the arrow, the user may press against the finger rest 134 to ratchet the second arm 130 away from the handle 110A. When the second arm 130 is fully released, the arms 120, 130 align, as shown in FIGS. 4 and 5B. The width of the instrument 100 in the released configuration is in the range of about 25-40 mm, and preferably about 32 mm.

Figure 7:
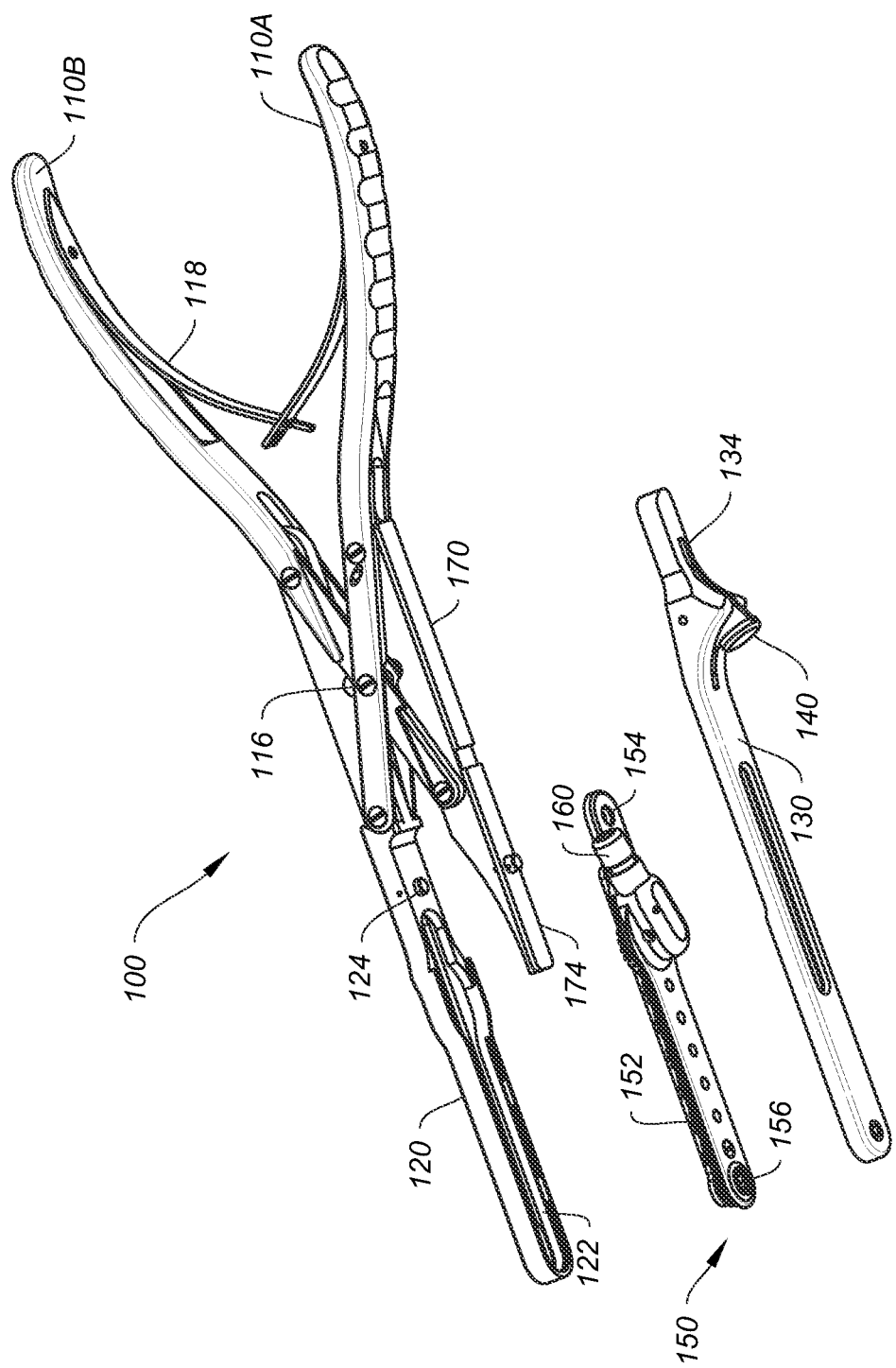
FIG. 7 is an exploded view of the bone fastener assembly instrument of FIG. 2.

As previously mentioned, the bone fastener assembly instrument 100 may be fully disassembled, as shown in FIG. 7, by depressing the release button 140 as well as the spring buttons 124, 174. This allows all of the components to be sterilized and then re-assembled for future use.

To assemble the system 10, the implantable device 20 is inserted between the spinous processes of adjacent vertebrae. Any appropriate surgical approach may be used to expose/visualize the spinous processes. After the implantable device 20 has been properly aligned so that the spinous processes seat securely within the stirrups 38 of the device 20, a hole can be punched through the apertures 50 of each of the pair of lateral walls 36, the apertures serving as a guide for placement of the hole through the spinous processes and allowing the bone fastener 60 to be positioned in the hole and through the spinous process. The holes may be formed using, for example, a hole puncher.

FIGS. 10A-10I illustrate an exemplary method of using the bone fastener assembly instrument 100 of the present disclosure to assemble the prior art bone fastener 60 through the implantable device 20 of the prior art. After sterilizing the instrument 100, the user attaches the components together by snapping the transmission mechanism 150 to the first arm 120, and snapping the second arm 130 to the rail 170. Next, the bone fastener 60 is loaded onto the instrument 100 in the expanded configuration, with the bolt 70 attached to the first component holding portion 156 of the transmission mechanism 150, and the nut 80 attached to the second component holding portion of the second arm 130.

Figure 10A:
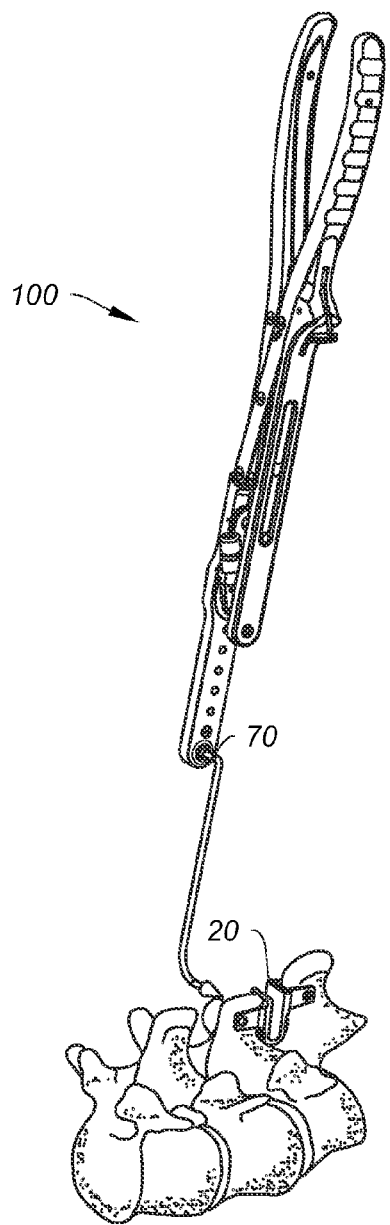
Figure 10B:
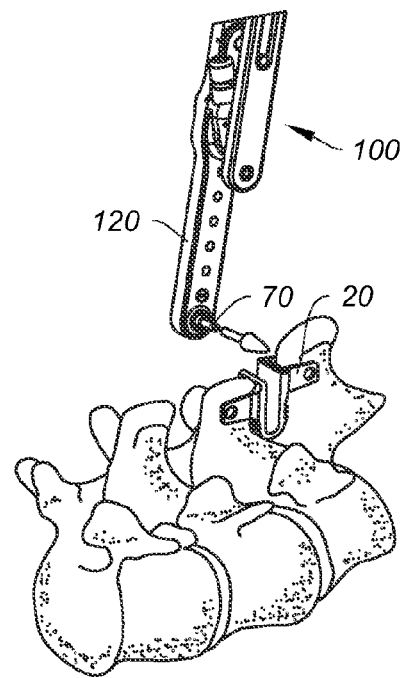
Figure 10C:
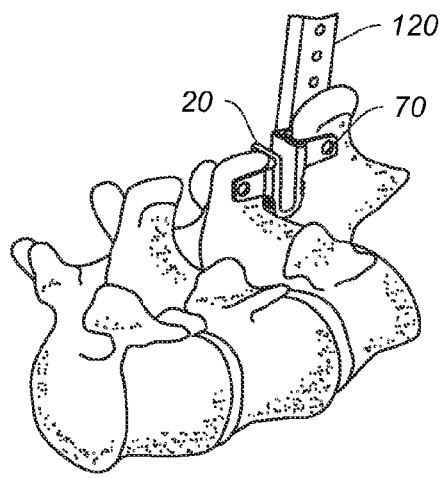

When the user is ready to assemble the bone fastener 60 together, the instrument 100 is first collapsed by sliding the arm 130 up to the end position, creating the slim profile configuration illustrated in FIG. 10A. In this collapsed configuration, the working ends of the arms as well as the handles are closed. With the bone fastener 60 loaded onto the instrument 100, the user introduces the bolt 70 with the first arm 120 toward the target site, which in this example is the aperture 50 of the implantable device 20. As indicated by the arrow in FIG. 10B, the user approaches the target site by aligning the attached bolt 70 to the target location. Thus, the instrument 100 allows a starting approach that only requires one arm to be aligned, and allows the ability to have the other arm positioned away from the active site to keep the area clear and allow maximum visibility and work space, as represented in FIG. 10C.

Figures 10D, 10E:
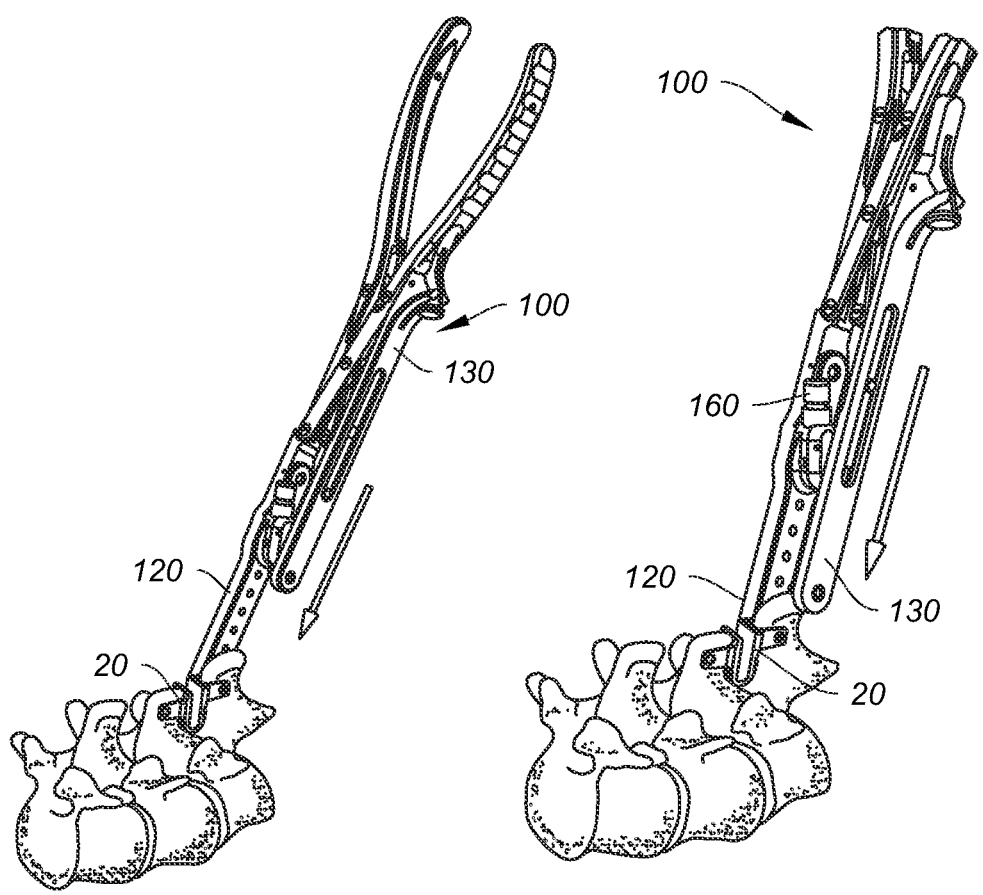

Once the first arm 120 is in position, the instrument 100 is released or expanded by sliding the second arm 130 down the end of the rail 170 to open up the working ends of the arms. As illustrated in FIGS. 10D and 10E, the second arm 130 may be slid down until the instrument 100 is fully expanded, thereby aligning the free ends of the arms 120, 130 and consequently the attached nut 80 with the attached bolt 70 on opposed sides of the implantable device 20, as shown in a different angle at FIGS. 10F and 10G.

Figures 10H, 10I:
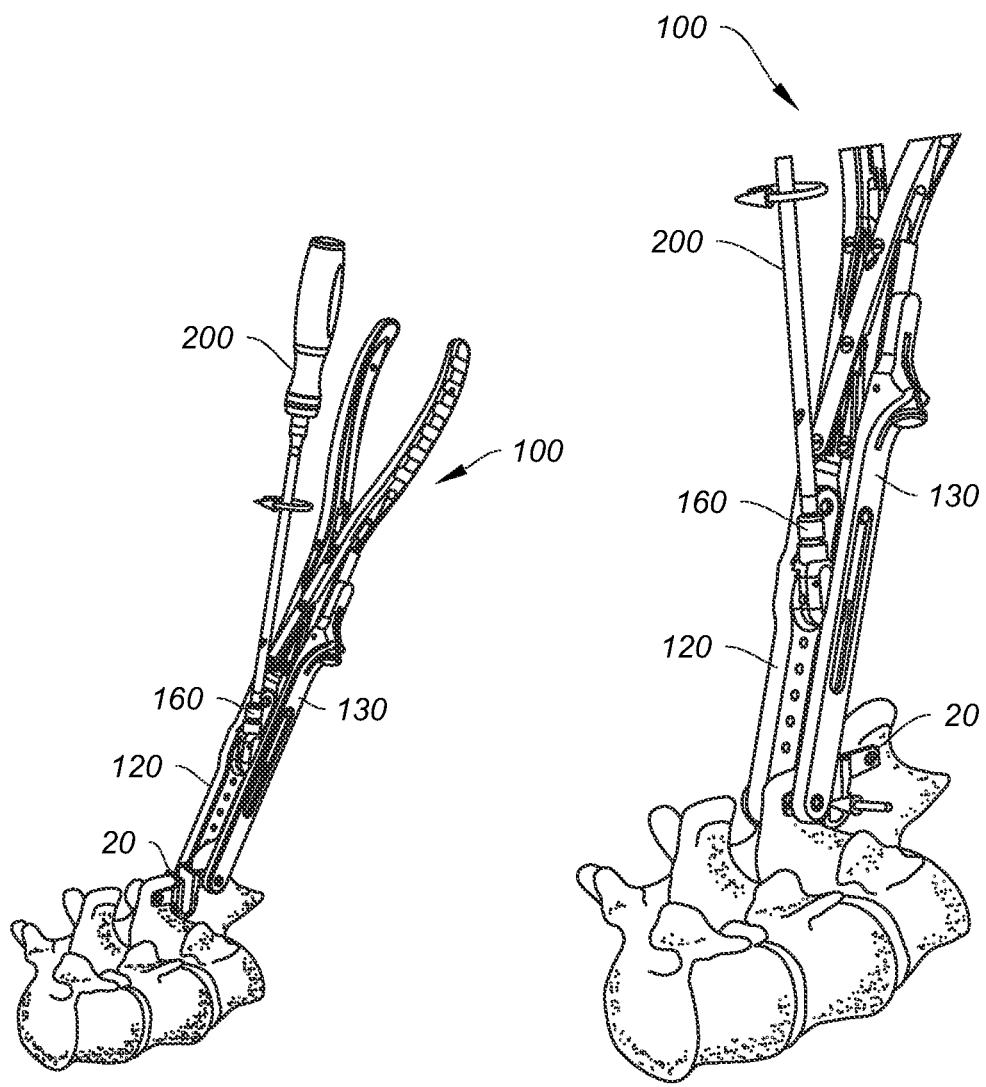

When it has been determined that the free ends of the arms are aligned and alignment of the bolt 70 and nut 80 is axially correct, a tightening instrument 200 of the kind described in U.S. Pat. No. 7,922,750 can be placed into the port 160. Turning the tightening instrument 200 causes the actuation of the transmission mechanism 150 and rotation of the bolt 70, thereby causing the threading of the bolt 70 into the nut 80, as shown in FIGS. 10H and 10I.

The assembly instrument 100 facilitates alignment and threading of the bolt 70 and nut 80. For example, since there may be limited space available on lateral sides of the walls 36, it may be difficult for a surgeon to position the bolt 70 and nut 80 through a spinous process. The assembly instrument 100 maintains the bolt 70 and nut 80 in the properly aligned position so as to ensure that they easily thread together during assembly, while also providing a space-saving solution of allowing one arm to be extended and one arm to be retracted in the initial approach. Further, the assembly instrument allows for quick rotation of the bolt 70 to secure the components to one another. A maximum of 7 to 10 rotations of the tightening instrument 200, and more preferably not more than 9 rotations, are required to complete the assembly process. The transmission mechanism 150 may be configured with an inside transmission ratio of 2:1, for example, for a very fast assembly time. Of course, other transmission ratios may be utilized as well.

In some embodiments, one or more additional instruments may be provided to assist in positioning the spinous processes of the vertebrae to be treated. For example, to properly implant the device 20 between spinous processes of the lumbar vertebrae, it may be desirable to position the patient in a certain degree of lordosis. However, during surgery, the patient may not be positioned ideally. Therefore, to assist the surgeon in producing the desired degree of lordosis, a pair of compression pliers may be provided.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An instrument for assembling a two-component bone fastener comprising:
    a pair of first and second handles, the first handle extending into a first arm and the second handle extending into a second arm, each arm terminating in a working end configured to hold a component of the bone fastener;
    a bias spring positioned between and contacting the first and second handles;
    a transmission releasably connected to the first arm and comprising a drive train for rotating one of the components; and
    a releasable catch between the first handle and the second arm for maintaining the second arm in a retracted position relative to the first arm during insertion and an expanded position relative to first the arm during assembly.

2. The instrument of claim 1, wherein the two-component bone fastener comprises a threaded bolt and threaded nut, and the working ends are configured to hold the threaded bolt and threaded nut in alignment.

3. The instrument of claim 1, wherein the bias spring comprises a leaf spring.

4. The instrument of claim 1, wherein the transmission is attachable to a cutaway portion in an inner wall of the first arm.

5. The instrument of claim 1, wherein the releasable catch comprises a ratcheting mechanism.

6. The instrument of claim 1, wherein the transmission and second arm can be disassembled from the remainder of the instrument.

7. The instrument of claim 6, further including a release button for disassembling the transmission and second arm from the remainder of the instrument.

8. The instrument of claim 1, wherein the transmission further includes a port for cooperatively receiving a tightening tool.

9. The instrument of claim 8, wherein the tightening tool actuates the transmission.

10. The instrument of claim 1, wherein the second arm is slidably connected to a rail extending from the first handle.

11. The instrument of claim 1, wherein each of the working ends includes a bone fastener component holding portion.

12. The instrument of claim 1, wherein the handles are attached at a pivotable hinge.

13. The instrument of claim 10, further including a finger rest for effecting sliding of the second arm relative to the rail.

14. The instrument of claim 1, wherein the transmission further comprises a series of gear wheels.

15. The instrument of claim 1, wherein the transmission further comprises a rollerchain.

* * * * *